(12) United States Patent
Yengoyan et al.

(10) Patent No.: US 6,953,520 B2
(45) Date of Patent: Oct. 11, 2005

(54) CAPILLARY ELECTROPHORESIS PROBES AND METHOD

(75) Inventors: Leon S. Yengoyan, San Jose, CA (US); Paul L. Frattini, Los Altos, CA (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 460 days.

(21) Appl. No.: 09/728,723

(22) Filed: Nov. 30, 2000

(65) Prior Publication Data

US 2002/0092768 A1 Jul. 18, 2002

Related U.S. Application Data

(60) Provisional application No. 60/168,427, filed on Nov. 30, 1999.

(51) Int. Cl.[7] ..................... G01N 27/447; G01N 27/453
(52) U.S. Cl. ..................... 204/452; 204/468; 204/603
(58) Field of Search .............................. 204/468, 450, 204/451, 452, 453, 600, 601, 603

(56) References Cited

U.S. PATENT DOCUMENTS

| | | | |
|---|---|---|---|
| 4,104,308 A | 8/1978 | Gadek et al. | 260/586 R |
| 4,340,595 A | 7/1982 | Franke et al. | 424/244 |
| 4,478,694 A | 10/1984 | Weinberg | 204/77 |
| 4,589,964 A | 5/1986 | Mayhan et al. | 522/85 |
| 4,828,983 A | 5/1989 | McClune | 435/7 |
| 5,069,766 A | 12/1991 | Zhu et al. | 204/454 |
| 5,104,506 A | 4/1992 | Jones et al. | 204/180.1 |
| 5,128,005 A | 7/1992 | Jones et al. | 204/180.1 |
| 5,156,724 A | 10/1992 | Jones et al. | 204/180.1 |
| 5,215,890 A | 6/1993 | Theodoropulos et al. | 435/28 |
| 5,288,811 A | 2/1994 | Brois | 525/383 |
| 5,366,601 A | 11/1994 | Jones et al. | 204/180.1 |
| 5,866,683 A | 2/1999 | Shimura et al. | 530/328 |
| 6,322,980 B1 * | 11/2001 | Singh | 435/6 |
| 6,331,235 B1 * | 12/2001 | Dolphin et al. | 204/451 |
| 6,511,850 B1 * | 1/2003 | Vigh et al. | 436/127 |

FOREIGN PATENT DOCUMENTS

| | | |
|---|---|---|
| JP | 06082423 A | 3/1994 |
| JP | 09325130 A | 12/1997 |
| JP | 10197481 A | 7/1998 |
| JP | 11118761 A | 4/1999 |

OTHER PUBLICATIONS

Macka et al. "Changes in Electrolyte pH Due to Electrolysis during Capillary Zone Electrophoresis," Anal. Chem., 70, p. 742–74 (Feb. 15, 1998).*

Fukushi et al. "Determination of ascorbic acid in vegetables by capillary zone electrophoresis," Journal of Chromatography A, 772, p. 313–320 (1997).*

Allinger et al., "Chromophoric Groups" and "Conjugated Systems," Organic Chemistry, 2nd Ed., p. 764–768 (1976).*

(Continued)

Primary Examiner—Alex Noguerola
(74) Attorney, Agent, or Firm—Morgan Lewis & Bockius, LLP

(57) ABSTRACT

A novel class of capillary electrophoresis probes and a method of employing the same are described. The novel class of capillary electrophoresis probes are comprised of one or more vinylogous carboxylic acid compounds or their derivatives. In another aspect of the present invention, a method of detecting ions in water by capillary electrophoresis is provided wherein: water is introduced into a capillary filled with an electrolyte which contains UV absorbing species comprised of one or more vinylogous carboxylic acid compounds. An electric voltage is applied along the capillary to cause ions present in the water to move along the capillary and separate. The ions displace the UV absorbing species and are detected indirectly by a UV/visible light photometric detector.

172 Claims, 1 Drawing Sheet

OTHER PUBLICATIONS

Tu et al., "The influence of fluorescent dye structure on the electrophoretic mobility of end–labeled DNA," Nucleic Acids Research, 1998, vol. 26, No. 11, 2797–2802.* http://www.whatislife.com/reader/dna–rna/dna–rna.html.*

"Organic Acids without a Carboxylic Acid Functional Group", G. V. Perez and Alice L. Perez, Journal of Chemical Education, vol. 77, No. 7, pp. 910–915 (Jul. 2000).

Oehrle, Stuart A., "*Controlled changes in selectivity of cation separations by capillary electrophoresis using various crown–ether additives*," Journal of Chromatography A, 745 (1996), pp. 87–92.

Doble et al., "*Design of background electrolytes for indirect detection of anions by capillary electrophoresis*", Trends In Analytical Chemistry, vol. 19, No. 1, 2000, pp. 10–17.

Ehmann et al., "*Capillary preconditioning for analysis of anions using indirect UV detection in capillary zone electrophoresis*", "*Systematic investigation of alkaline and acid prerinsing techniques by designed experiments*", Journal of Chromatography A, 816 (1998), pp. 261–275.

Fritz, James S., "*Recent developments in the separation of inorganic and small organic ions by capillary electrophoresis*", Journal of Chromatography A, 884 (2000), pp. 261–275.

Pacáková et al., "*Capillary electrophoresis of inorganic anions and its comparison with ion chromatography*," Journal of Chromatography A, 789 (1997), pp. 169–180.

* cited by examiner

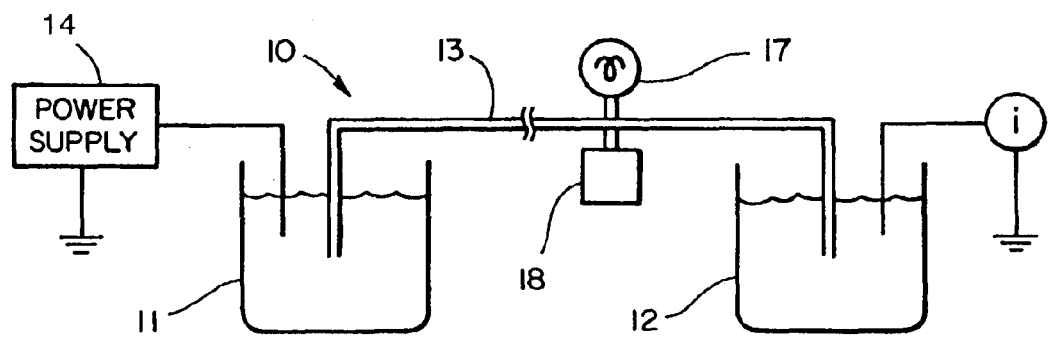
FIG_1
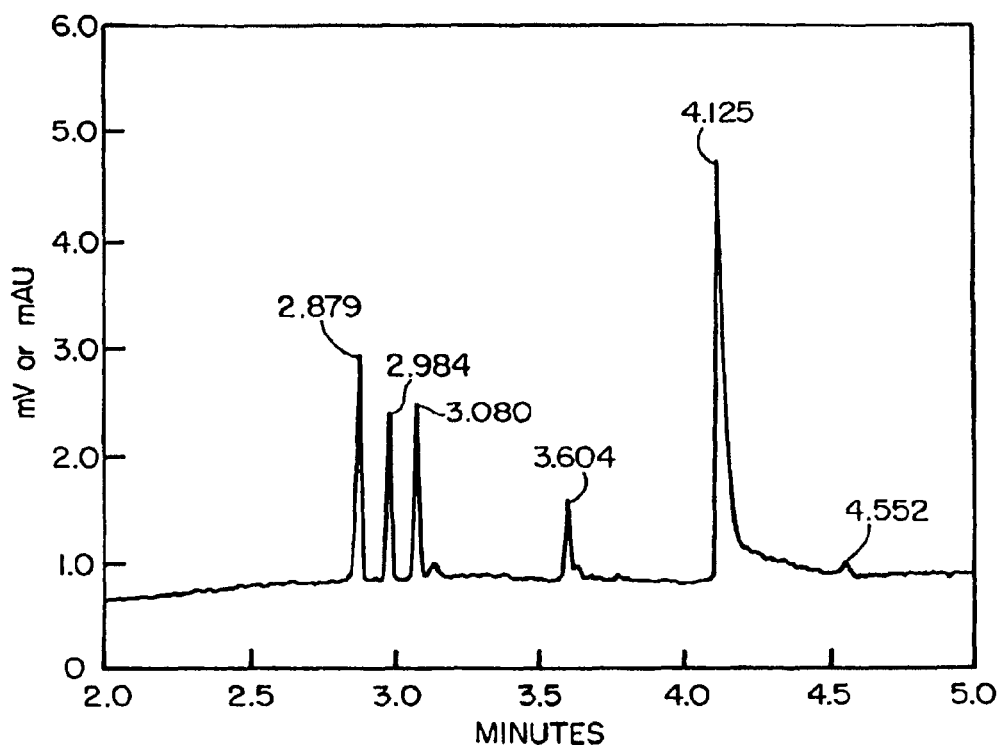
FIG_2

CAPILLARY ELECTROPHORESIS PROBES AND METHOD

This application claims priority from provisional application No. 60/168,427, which was filed on Nov. 30, 1999.

BRIEF DESCRIPTION OF THE INVENTION

This invention relates generally to probes for capillary electrophoresis and a capillary electrophoresis method. More particularly, the present invention relates to a class of novel capillary electrophoresis probes comprised of vinylogous carboxylic acid compounds and derivatives, and a capillary electrophoresis method employing the same.

BACKGROUND OF THE INVENTION

Ultrapure water, that is water with a low concentration of ionic species, is required in many industrial processes. For example, ultrapure water is required in the processing of semiconductor devices to produce defect free devices. Other industries that requires ultrapure water are the pharmaceutical, agricultural, chemistry and food industries. Ultrapure water is also required in nuclear reactors, particularly for the prevention of corrosion. The monitoring of ionic species in water in light water reactors (LWR) such as pressurized water reactors (PWR) and boiling water reactors (BWR), is essential to control corrosion. Monitoring of ionic species in nuclear power plants must be able to monitor very low concentrations, in some applications at concentrations as low as parts-per-trillion (ppt).

Conductometric and photometric detection has been employed to detect the presence of ionic species in water. Currently, virtually all nuclear plants use in-line Ion Chromatography (IC) for routine monitoring of ionic species. The high cost of consumables together with the large sampling volumes that are required and the long analysis times inherent to IC monitoring provides considerable incentive to develop alternative measuring or monitoring methodologies.

One such alternative methodology is Capillary Electrophoresis (CE), which employs 10 to 100 times lower eluent volumes and provides an order of magnitude quicker measurement time (typically less than a three minute compared to 15 to 30 minutes or more for IC). Further, CE requires three to six orders of magnitude less analysts sample, which is particularly attractive to analysis of nuclear reactor water given the escalating radiation waste costs. CE is also capable of simultaneous transition metal cation separations not easily done by IC. A general discussion of CE can be found in the textbook *Capillary Electrophoresis of Small Molecules and Ions*, Peter Jandik, Gunther Bonn, 1993, Chapter 3 in particular.

Much effort has been focused on the development of CE systems. Jones et al describes in U.S. Pat. No. 5,566,601 a technique for separating, identifying and measuring ions in solution by capillary zone electrophoresis, which provides improved sensitivity and resolution of ionic species. The method involves introducing a sample containing the ionic species into a narrow bore capillary filled with a carrier electrolyte containing a selected visible or UV-absorbing anion or probe. An electrical potential is applied across the capillary column causing the ions to elute according to their mobility. Both ultraviolet (UV) absorbing and UV-transparent ions can be detected and quantitated by UV/visible photometric monitoring. They suggest using as the light-absorbing anion, one selected from molybdate, tungstate, ferrocyanide, ferricyanide, bromide, iodide and dichromate as examples.

As has been discussed in the literature, one aspect of development of CE systems has focused on the selection of the probe used in CE. When detection of inorganic or small molecular weight organic species (i.e. the "species of interest" or analysts) that lack appreciable absorbance, CE detection is typically performed by indirect detection using a background electrolyte (BGE) containing a UV absorbing species—also referred to as the probe. The UV transparent analysts is detected by displacement of the probe by the analysts.

It is suggested that a number of factors are important in selection of the probe. First the electrophoretic mobility ($\mu$) of the probe is considered and should be closely similar to the mobilities of the analytes of interest. Second the minimum detectable concentration $c_{lim}$ of the CE system is considered, and is established by the following relationship:

$$c_{lim}=c_m/(TR \times DR), \tag{1}$$

where $c_m$ is the concentration of the probe, TR is the transfer ratio, and DR is the dynamic reserve which is a measure of the ratio of the signal to noise for a given signal. The transfer ratio is the number of equivalents of the probe ions that will be displaced by each equivalent of analysts ions. For example, a common probe pyromellitic acid, when totally ionized, has a transfer ratio of 0.25 for mono-valent ions, and 0.5 for divalent ions. The dynamic reserve is given by the relationship:

$$DR=(\epsilon \cdot L \cdot c_m)/AN \tag{2}$$

where $\epsilon$ is the molar absorptivity of the probe, L is the path length of the light through the capillary, and AN is the absorbance noise level which is a function of the detector wavelength. Substituting for DR in Equation 2 into Equation 1, the following expression for the minimum detectable concentration is obtained:

$$c_{lim}=AN/(\epsilon \cdot L \cdot TR) \tag{3}$$

A general discussion of these principles and equations may be found in *Capillary Electrophoresis of Small Molecules and Ions*, Peter Jandik, Gunther Bonn, 1993, Chapter 3, and particularly at pages 134–150.

Many probes have been taught in the prior art. For example, U.S. Pat. No. 5,128,005 teaches using a chromate ion. U.S. Pat. No. 5,156,724 teaches using a UV-absorbing amine or heterocyclic sulfate compound. U.S. Pat. No. 5,104,506 teaches using a chromate salt and an alkyl quaternary ammonium salt. Another probe which has been used in the prior art for indirect detection in CE is the aromatic compound pyromellitic acid.

In general, a number of criteria for a successful probe have been discussed in the prior art. Specifically, it is important for the mobility of the analysts to match the mobility of the probe. High molar absorbtivity of the probe is also important. The detector wavelength at which high molar absorbtivity is exhibited by the probe is another important criteria. For example, it is beneficial for the detector wavelength to be a value that minimizes the AN, and which avoids conflict with absorbance bands of the analytes. Finally, the solubility of the anion probe is important when reverse electro-osmotic flow (EOF) modifiers are used in order to avoid precipitation. For probes with low molar absorbtivity, higher probe concentrations are required to obtain satisfactory minimum detectable analysts concentration. The higher probe concentrations can result in potential problems by "probe induced" precipitation of the dynamic EOF modifiers within the capillary. A general discussion of these and other criteria can be found for example in James S. Fritz, *Recent developments in the separation of inorganic and small organic ions by capillary electrophoresis*; J. of Chromatography A, 884 (2000) 261–275; and Philip Doble, Miroslav Macka, Paul R. Haddad, *Design of background electrolytes for indirect detection of anions by capillary electrophoresis, Trends in Analytical Chemistry*, vol. 19, no. 1, 2000, pgs 10–17.

While much effort has been focused on the development of probes, the prior art probes available to date are not entirely satisfactory. Contrary to the desired criteria as discussed above, it turns out that many of the prior art probes exhibit strong absorbance in the low UV spectrum, i.e. the detection wavelength, and this is the very region where the analytes or species of interest also exhibit strong absorbance. This similarity in absorbance of the analytes of interest makes indirect detection of analytes difficult. Also, the absorbance noise is elevated at these lower wavelengths, thereby decreasing dynamic reserve. In addition, the minimum detectable concentration $c_{lim}$ is often too high for many applications in the semiconductor, nuclear power and other industries due mostly to low molar absorbtivity $\epsilon$ at otherwise optimum detection wavelengths. Further, multi-ionized probes such as pyromellitic acid have low transfer ratios which lead to higher minimum detectable concentrations. Additionally, such probes are typically useful in detecting only a small range of analytes, and are not applicable to a wide range of applications. Accordingly, continued development of improved probes and CE methods are of interest.

SUMMARY OF THE INVENTION

In general it is an object of the present invention to provide a class of novel capillary electrophoresis probes, and a capillary electrophoresis method employing the same.

The inventors have discovered a novel class of capillary electrophoresis probes comprised of one or more vinylogous carboxylic acid compounds. In particular, vinylogous carboxylic acid compounds of the present invention are defined as compounds containing one or more enol functional groups in conjugation with one or more carbonyl functional groups through one or more carbon-carbon or carbon-nitrogen double bonds. Preferably, the vinylogous carboxylic acid compounds of the present invention are cyclic compounds. The vinylogous carboxylic acid compounds of the present invention further include tautomers, in particular keto-enol tautomers. The vinylogous carboxylic acid compounds of the present invention further include compounds where the aforementioned conjugation is obtained through one or more stabilized resonance forms of an aromatic compound. The vinylogous carboxylic acid compounds of the present invention may alternatively be cationic compounds, that is, positively charged by employing a positively charged group(s). In one example, the cationic compound includes cationic ester derivatives of the vinylogous carboxylic acid compounds. In another example, the cationic compound includes cationic amide derivatives of the vinylogous carboxylic acid compounds.

In another aspect of the present invention, a method of detecting ions in water by capillary electrophoresis is provided wherein: water is introduced into a capillary filled with a background electrolyte having some water which contains UV absorbing species or probe comprised of one or more vinylogous carboxylic acid compounds. An electric voltage is applied along the capillary to cause ions present in the water to move along the capillary and separate. The ions displace the UV absorbing species and are detected indirectly by a UV/visible light photometric detector.

In yet another aspect of the present invention a capillary electrophoresis apparatus is provided in which a background electrolyte containing one or more probes or alternatively a combination of one or more probes and a buffer are placed in the capillary, and the one or more probes are comprised of one or more vinylogous carboxylic acid compounds.

In a further aspect of the present invention, a kit containing one ore more reagents for performing capillary electrophoresis is provided wherein the one or more reagents include one or more probes comprised of one or more vinylogous carboxylic acid compounds. Alternatively, the reagents may also include one or more buffer solutions.

BRIEF DESCRIPTION OF THE DRAWINGS

The invention will be more clearly understood from the following detailed description when read in conjunction with the accompanying drawings in which:

FIG. 1 is a schematic diagram of a capillary electrophoresis apparatus which may be employed with the capillary electrophoresis probe and method of the present invention.

FIG. 2 is a electropherogram showing the separation of five anions by capillary electrophoresis (CE) using a squaric acid buffer according to one embodiment of the present invention.

DETAILED DESCRIPTION OF THE INVENTION

The inventors have discovered a novel class of UV absorbing species or probes for use in capillary electrophoresis (CE) and a method employing the same. It should be understood that the terms probe and UV absorbing species are synonyms and may be used interchangeably throughout the present description. In particular, the capillary electrophoresis probes of the present invention are comprised of one or more vinylogous carboxylic acid compounds. The suitability of these compounds as probes in CE was unexpected. In particular, vinylogous carboxylic acid compounds of the present invention are defined as compounds containing one or more enol functional groups in conjugation with one or more carbonyl functional groups through one or more carbon-carbon or carbon-nitrogen double bonds. A general description of vinylogous carboxylic acid compounds may be found in G. V. Perez and Alice L. Perez, *Organic Acids without a Carboxylic Acid Functional Group*, J. of Chemical Education, Vol. 77, No. 7, July 2000, pgs. 910–915. Preferably, the vinylogous carboxylic compounds of the present invention are cyclic compounds. Also it should be understood by those of skill in the art that the vinylogous carboxylic acid compounds of the present invention include tautomers of other structures which have undergone keto-enol tautomerization. Also, it should be understood by those of skill in the art that the vinylogous carboxylic acid compounds of the present invention include aromatic structures. As described further below, the vinylogous carboxylic acid compounds of the present invention may be either anionic and cationic. This allows the detection of both anion and cation analytes.

The vinylogous carboxylic acid compounds of the present invention are conjugated. Conjugation may take two forms. First, conjugation may occur through one or more carbon-carbon or carbon-nitrogen double bonds, i.e. linear conjugation. Alternatively, conjugation may occur through an aromatic system when one or more stabilized resonance structures of the aromatic compounds are vinylogous carboxylic acids. Linear and aromatic conjugation may also occur in compounds containing heteroatoms. When conjugation occurs through either an aromatic system or a hetero aromatic system, suitable compounds according to the present invention will produce stabilized resonance structures.

Representative examples of probes of the present invention comprised of vinylogous carboxylic acid compounds include, but are not limited to the following compounds: 3,4-dihydroxy-3-cyclobutene-1,2-dione (squaric acid); 2,5-dihydroxy-1,4-benzoquinone; 4,5-dihydroxy-4-cyclopentene-1,2,3-trione (croconic acid); 2-hydroxy-2,4,6-cycloheptatrienone (tropolone); 6-hydroxy-1-tetralone and 5,5-dimethyl-1,3-cyclohexanedione (dimedone). These compounds are illustrated as:

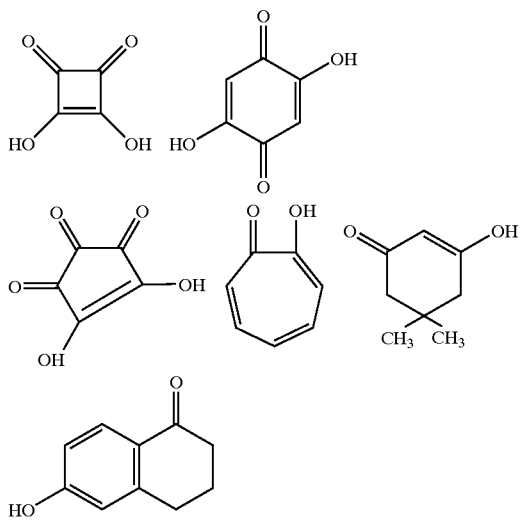

The inventive compounds include peripheral substitution which does not alter the vinylogous carloxylic acid UV-chromophore as shown for the example below:

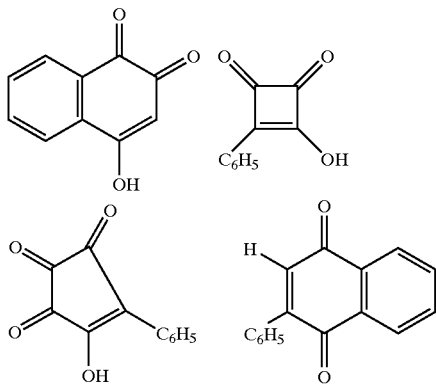

Other examples of compounds which fit the definition of the present invention further include: 5,6-dihydroxy-5-cyclohexene-1,2,3,4-tetraone (rhodizonic acid); 2-hydroxy-1,4-napthoquinone; 3-oxogulofuranolactone; 2,2-dimethyl-1,3-dioxane; 4,6-dione-4-ketobutyrolactam; tetrahydrofuran-2,4-dione; 2,3-dihydroxy-2-cycloprofenegne (deltic acid) and uric acid. As described above, embodiments of the invention include tautomers, in particular keto-enol tautomers. One example of the keto-enol tautomerization equilibria in accordance with the present invention is shown below:

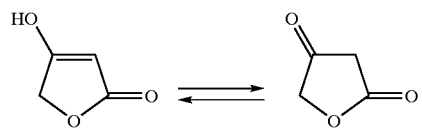

Also, as described above, one embodiment of the present invention includes conjugation through an aromatic structure where the vinylogous carboxylic acid is one stabilized resonance form. One example of this is shown below:

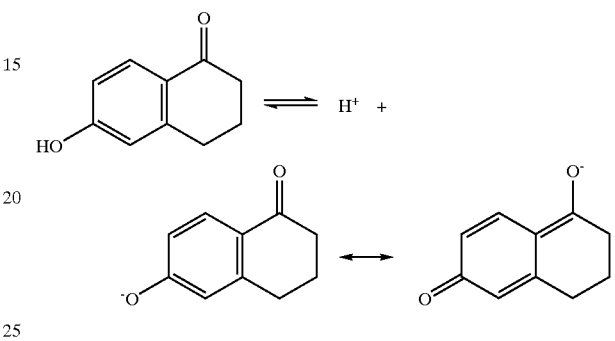

Of particular advantage, the vinylogous carboxylic acid compounds of the present invention may alternatively be positively charged by employing a positively charged group. Examples of such cationic vinylogous carboxylic acid derivatives include cationic ester derivatives of the vinylogous carboxylic acid compounds. One example of such ester derivative compounds is an ester derivative of squarate, shown below as:

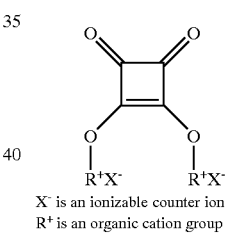

X⁻ is an ionizable counter ion
R⁺ is an organic cation group

In another embodiment the cationic vinylogous carboxylic acid derivatives include cationic amide derivatives of the vinylogous carboxylic acid compounds. One example of such amide derivative compounds is an amide derivative of squarate, shown below as:

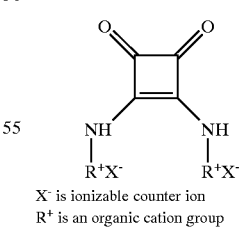

X⁻ is an ionizable counter ion
R⁺ is an organic cation group

The probes of the present invention may be combined with a buffer to provide the capillary electrophoresis background electrolyte (BGE). Alternatively, the BGE may include only the probe without the buffer. When a buffer is used, examples of a suitable buffer for use with the present invention include, but are not limited to: tris base, amines and organic bases. The probes of the present invention are usually present in the BGE in a concentration in the range of about 2 to 5 mM, more usually in the range of about 2.5 to 3.5 mM. The BGE generally has a pH in the range of about 7 to 10, however it can be as low as 2–3.

The BGE may also include a dynamic electroosmotic flow modifier in addition to the probe; however this is not necessary. A flow modifier acts to stop or reverse the electro osmotic flow EOF of the carrier electrolyte. Examples of suitable dynamic flow modifiers for use with the present invention include cetyltrimethylammonium bromide (CTAB) and didodecyldimethylammonium bromide (DDAB). The BGE may also include some organic solvent that is mixable with the water of the buffer. Such solvents can be methanol, ethanol and acetone as examples.

Of particular advantage, the present invention promotes improved CE measurements, and allows the application of CE to new fields heretofore unavailable due to detection level limits. These new industries include nuclear power water chemistry and semiconductor processing water chemistry applications, among others. Specifically, the vinylogous carboxylic acid compound probes of the present invention possess mobilities ($\mu$) that are comparable to the analytes of interest. Their molar absorbtivity is high. The transfer ratio can be higher (i.e. $SO_4^{2-}$ to $PMA^{4-}$). The absorbance noise is lower at higher wavelengths, and analysts interference is lower at the higher wavelength. Further, the problems of EOF precipitation are absent.

One example of anion analysts species of interest detected by the present invention include bromide, chloride, fluoride, nitrate, nitrite, sulfate, phosphate and the like including small molecular weight organic anions. In an alternative embodiment, the vinylogous carboxylic acid compound is positively charged and is suitable for detection of cation analytes such as $Na^+$, $K^+$, $Mg^{+2}$, and $Ca^{+2}$, and small molecular weight organic cations.

Of further significant advantage, the probes of the present invention exhibit high molar absorbtivities in the high UV spectrum region of the photometric detector. As described above in the Background, one of the unsatisfactory aspects of prior art probes is their strong absorbtivity in the similar region of absorbance of the analytes. In contrast, the probes of the present invention exhibit higher molar absorbtivity in a higher UV region than most analytes and this provides for increased detection and sensitivity of the CE system. In general, the vinylogous carboxylic acid compounds of the present invention exhibit molar absorbtivity at wavelengths of about 270 nm and higher. In one embodiment where the probe is squaric acid (SQ), for example, SQ is found to exhibit high molar absorbtivity at a wavelength of about 270 nm. In another example where the probe is 2,5-dihydroxy 1,4-benzonquinone (BZ), BZ is found to exhibit high molar absorptivity at a wavelength of about 320 nm. As shown further below in the experiments, these wavelength values are much higher than conventional probes such as pyromellitic acid (PMA) which typically exhibit high molar absorbtivity at a wavelength of about 214 nm. It should be pointed out that it is not just the wavelength value that is of significance; it is the fact that the probes of the present invention exhibit high molar absorptivity at these higher wavelengths. For example, PMA does show some molar absorbtivity at 270 nm, however it is a fraction of its value and will not provide the level of detection and/or sensitivity achieved by the present invention. For example, as shown below in the experiments, chromate, a conventional probe also exhibits molar absorbtivity at 270 nm and higher, but again its value is a fraction of that exhibited by the inventive probes at this wavelength. The higher molar absorbtivity exhibited by the inventive probes at the higher detection wavelength allows operation with greater dynamic reserve with higher molar absorbtivity since AN decreases with increasing wavelength. As shown in Equations 1 and 2 above, a greater dynamic reserve (DR) will result in a lower minimum detectable concentration c,i., and thus produces a more sensitive CE device and method. Further as described above, this higher detection wavelength of the inventive probes is above the absorbing wavelength of the analytes, and thus the inventive probes do not have the interference problems seen with prior art probes.

The present invention may be carried out in an CE system such as that illustrated in the schematic diagram of FIG. 1. The CE system 10 includes two reservoirs 11, 12 which are filled with the same BGE solution as the capillary 13 which extends between the two reservoirs. A high voltage is applied along the capillary by a suitable voltage source 14. The capillaries generally have a small internal diameter, typically 5–100 micrometers, to permit heat dissipation. The capillaries are generally made of fused silica. Ions are separated on the basis of their net electrophoretic mobilities. A detector assembly, in the present invention a UV/visible light detector assembly, is placed along the capillary. The detector assembly generally comprises a source of light 17 which directs a beam through the capillary to a detector 18. The light is absorbed by the ions passing between the light source 17 and the detector 18. The output signal is dependent on the degree of absorption of the light by the ions and the path length of the light through the electrolyte. The capillary is filled with the BGE containing the probes, and alternatively the probes and buffer, and ions are separated on the basis of their relative charge and hydration volume. In one embodiment, fused silica capillaries are employed, an electrical double layer is produced at the capillary surface due to the attraction of positively charged cations in the BGE to the ionized silanol groups on the capillary wall. In the presence of an electric field, the cations in the diffuse portion of this double layer move toward the cathode and drag the electrolyte bulk liquid with them, producing a cathodal electro osmotic flow. Alternatively, an anodal flow capillary may be used which is prepared by either use of dynamic EOF modifier static coating to produce an anodal electro-osmotic flow.

Most of the analysts ions of interest do not absorb light and they cannot be detected by the photometric detector. Thus, indirect photometric detection is used. The UV-transparent analysts ions are detected as zones of decreased absorbance or voids due to the displacement of the UV-absorbing species of the probe by the UV-transparent analysts ions. This process of indirect photometric detection is well-known; however, as described above, the prior art probes used for indirect detection do not have a sufficiently high UV molar absorptivity to permit detection of analysts ions in the low concentrations required for water testing in applications where ultrapure water is required.

We have found that in order to achieve detection of inorganic anions at very low levels, for example as low as in the 500 ppt ranges, the usual cathodal electro osmotic flow must be reversed, preferably without the use of modifiers in the BGE. In one embodiment of the present invention this is accomplished by treating the inside surface of the capillary to mask the free silanol group by applying a coating. Reverse electro osmotic flow capillaries for use in the present invention are available from Metachem, Los Angeles, Calif.

In an exemplary embodiment of the present invention, squaric acid (SA) is the preferred probe. Features making SA advantageous include: a) higher molar absorbtivity than pyromellitic acid at 270 nm, b) electrophoretic mobility comparable to low formula weight inorganic anions, c) double the transfer ratio for fully ionized squarate compared to fully ionized pyromellitic acid, and d) higher detector wavelength at peak absorbance.

Experimental

A wide range of experiments were performed to demonstrate the new CE probe and method. The following experiments are provided for purposes of teaching and illustration only, and are not intended to limit the scope of the present invention in any way. Various aspects were tested as shown below in the titled sections.

CE System

Experiments were performed with the capillary electrophoresis apparatus. The apparatus included a 75 micron capillary with an effective length of 35 cm and total length of 43 cm with positive wall surface (anodal EOF). Squaric acid was employed in a BGE, with added tris base and the concentration of the squaric acid was 2.5 mM and giving a BGE pH of about 8.0. The BGE was filtered through 0.45 micron membrane. Injections were electrokinetic (5 to 15 sec at –10 KV) and hydrodynamic (at 3–10 sec at 12 psi) with running voltage of –25 KV generating about 11–12 uamps in all runs with a field strength of 581 volts/cm. The capillary was maintained at 25° C. Detection was monitored indirectly with wavelength set for maximum absorbance at about 270 nm.

Ion analysis was performed using an analysts with 5 anion salt matrix with each salt at ppb concentrations as shown below in Table 1:

TABLE 1

| Analyte Compound | Concentration (ppb) |
|---|---|
| sodium chloride($Cl^-$) | 160 |
| sodium bromide ($Br^-$) | 160 |
| sodium sulfate ($SO_4^{-2}$) | 160 |
| sodium fluoride ($F^-$) | 80 |
| disodium phosphate ($HPO_4^{-2}$) | 320 |

The results of the analysis are illustrated in the electropherogram of FIG. 2, and show separation of all anions within two-and-a-half minutes after injection, with peak signals considerably higher than the background. The test conditions were: 2.5 mM tris squarate, pH=8, 10 second hydrodynamic injection, –25 KV, 25° C., detector at 270 nm, current 7.1 μamps, using a Spectophoresis 1000 CE system. The elution order of the ions is $Br^-$, $Cl^-$, $SO_4^{-2}$, $F^-$ and $HPO_4^{-2}$. Although a baseline drift is observed, other results have shown stable baselines and this non-optimized method appears to be reproducible and robust.

The CE probes and method of the present invention may be employed with any suitable type of CE system. Given the teaching of the present invention, each CE system may be optimized using routine experimentation within the skill of the art; and for example may include: a) optimizing capillary length and effective length for peak resolution to maximize separation, driving voltage with minimum current b) optimizing BGE concentration and capillary diameter for signal-to-noise, and examine effect of pH on BGE sensitivity c) optimizing electrokinetic injection voltage and voltage application time and hydrodynamic injection d) optimizing injection buffer for transporting the analysts to the BGE interface via isotachophoretic stacking, e) employing bubble, "L" or "Z" cell detector geometries to obtain an increase in detector signal by a factor of 2 to 10, f) obtain positively identifiable standard peaks using single analysts buffer standards g) eliminating carbon dioxide contamination from air by using on-line sample delivery from high purity water source, and h) study the effect of counter ion of the probe.

Experimental Mobilities

The mobilities of certain vinylogous carboxylic acid compounds of the present invention were experimentally evaluated. Specifically, squaric acid and 2,5 dihydroxy 1,4 benzoquinone, along with conventional probes, chromate ion and pyromellitic acid, were experimentally measured. These compounds represent a high calculated charge to mass ratio. A capillary having anodal EOF was used. These compounds have coelectro-osmostic flow. Each compound was run in the presence of the neutral marker, benzyl alcohol. The buffer of the present invention was 20 mM tris chloride at pH=8.0. The sample buffer for chromate and pyromellitic acid was also 20 mM the tris chloride buffer, pH=8. Since squaric acid and 2,5 dihydroxy 1,4 benzoquinone are acidic, each sample was neutralized with 0.1 M NaOH to pH of 7.0. Prior work showed that these two compounds electrophoresed poorly if the tris chloride buffer was used to dissolve the samples as the pH was still acidic causing the injection front to deteriorate during the run.

The mobilities were calculated as follows:

$$u^{obs} = eof + u^{true}$$

where $u^{true}$ is the actual mobility of the probe under the stated conditions, the observed mobility $u^{obs}$ and eof were measured by the equation:

$$u^{obs} = (I)(L)/(V)(t)(60)$$

where I is the effective length of the capillary, L is the total length of the capillary, V is the voltage across the capillary and t is the time in minutes for the samples to pass the detector window. The eof is calculated by the same equation and the time is obtained from the neutral marker (benzyl alcohol) and the true mobilities are calculated as the difference between $u^{obs}$ and eof. Mobilities have a negative sign by convention because the osmotic flow and probe migration are to the anode for both.

The true mobilities are shown in Table 2 as:

TABLE 2

| true mobilities ($cm^2$/volt sec) | |
|---|---|
| chromate | $-7.96 \times 10^{-4}$ |
| pyromellitic | $-6.12 \times 10^{-4}$ |
| squaric acid | $-5.45 \times 10^{-4}$ |
| 2,5 dihydroxy 1,4 benzoquinone | $-2.01 \times 10^{-4}$ |

Comparing the experimental probe mobilities with literature values can be used only in a general sense as the mobilities of the probes are a function of pH, buffer, and buffer ionic strength effects. A brief comparison is shown in Table 3, where the probes are listed in decreasing order of mobilities.

| Inventors Experimental | Soga[1] | Haddad[2] |
|---|---|---|
| chromate | chromate | chromate |
| PMA | PMA | PMA |

-continued

| Inventors Experimental | Soga[1] | Haddad[2] |
|---|---|---|
| squarate | | |
| benzoquinone | | |

Soga[1]: Tomoyashi Soga, Gordan Ross, J. of Chrom. A, 767 (1997), pgs. 223–230;
Haddad[2]: Philip Doble, Miroslav Macka, Paul R. Haddad, Trends in Analytical Chemistry, Vol. 19, No. 1 (2000) pgs. 10–17.
PMA is pyromellitic acid and benzoquinone is 2,5 dihydroxy 1,4 benzoquinone.

As demonstrated by the above, the probes of the present invention exhibit sufficient mobilities for low and high mobility anions, as well has having the added advantage of exhibiting high molar absorbtivities in the high UV spectrum region of the detector where there is less interference with other absorbing analytes and where the detector shows more stable baseline producing a better signal to noise ratio. A comparison of the molar absorptivity and wavelength values for probes of the present invention compared to conventional probes are shown in Table 4 below:

TABLE 4

| Probe | Molar Absorbtivity ($M^{-1}cm^{-1}$) | Wavelength (nm) |
|---|---|---|
| squaric acid | 26,942 | 270 |
| benzoquinone | 30,347 | 320 |
| PMA | 23,088 | 214 |
| | 2,577 | 270 |
| chromate | 5,089 | 205 |
| | 4,585 | 274 |
| | 5,864 | 374 |
| trimesic acid | 37,144 | 209 |
| ortho phthalic acid | 13,812 | 208 |

While some of the conventional probes have high molar absorbtivity it should be recognized as described above that it is high in the UV region where interference will occur with the absorbtion spectrum of the analytes.

Evaluating Noise as a Function of Wavelength with Absorbing Probes

Three probes, two of the present invention and one conventional probe were tested to evaluate noise of the detector. PMA at a concentration of 7.3 mg/100 of tris chloride (pH=8.0) was pumped into a 75 micron capillary after the instrument was zeroed with the buffer only. The probe solution was very slowly passed through the solution producing an absorbance of 0.02548. This baseline noise was measured repeated with squaric acid and 2,5 dihydroxy 1,4 benzoquinone, with similar absorbance magnitude as shown in Table 5:

TABLE 5

| Probe | Wavelength (nm) Measured | Initial Absorbance | Concentration (mg/100 ml) |
|---|---|---|---|
| PMA | 214 | 0.02548 | 7.3 |
| squaric acid | 270 | 0.03187 | 3.6 |
| benzoquinone | 320 | 0.03290 | 4.5 |

The noise was evaluated over a period of 15 minutes by measuring the high and low amplitude signal as a function of voltage. The noise for the conventional PMA probe is roughly twice that of the inventive probes squaric acid and benzoquinone. These results confirm that the capillary detector as a spectrophotometer is less noisy at higher wavelength in the UV region, and thus the inventive probes provide this additional advantage as they are used at the higher wavelengths.

Evaluating Detector Noise and Drift

Experiments were conducted to evaluate detector noise and drift at four wavelengths. No probes were used. A capillary was filled with DI water with very low flow to prevent any heating in the capillary window. The absorbance was set to zero at 0.02 AUFS. The initial wavelength was at 214 nm for seven minutes, and then set to 254 nm with automatic zeroing for another 7 minutes, and then reset to 270 nm with automatic zeroing for another 7 minutes, and finally at 320 nm. At each wavelength there was a downward drift of the absorbance as you go from 214 nm to 320 nm, but the drift decreased at each new wavelength setting.

The evaluated noise at the four wavelengths was found at 214 nm to be twice as high as at the 254, 270 and 320 nm wavelength values. Thus, again the inventive probes which exhibit high molar absorbtivity at the higher wavelengths are being used at wavelengths having less detector drift.

As demonstrated by the above results, a useful improved probe for CE has been developed. In summary, the inventive probes exhibit mobility that substantially matches that of the ions of interest. The inventive probes exhibit high molar absorbtivity and higher transfer ratios which provides great potential for improving sensitivity beyond the existing art; and further greatly expands the utility of CE to new industries and applications requiring lower minimum detectable analysts concentration. Further, the inventive probes allow higher detection wavelengths giving higher absorbance values which provides the dual benefit of lower absorbance noise (AN) and less interference with the absorbance of the analytes. Finally, the inventive probes are less likely to adversely preciptiate anodal flow EOF modifiers because their high molar absorbtivity allows their use at low concentration.

The foregoing description of specific embodiments and examples of the present invention have been presented for the purpose of illustration and description. While the present invention has been described with reference to a few specific embodiments, the description is illustrative and is not to be construed as limiting the invention. Various modifications may occur to those of ordinary skill in the art without departing from the spirit and scope of the invention.

We claim:

1. A background electrolyte solution for detecting ions in a sample using capillary electrophoresis comprising:
 a capillary electrophoresis probe that is comprised of at least one vinylogous carboxylic acid compound or derivative thereof in a concentration of about 2 to 5 mM, wherein said vinylogous carboxylic acid compound is not tropolone.

2. The background electrolyte solution of claim 1 wherein said at least one vinylogous carboxylic acid compound has a structure comprising: one or more enol functional groups in linear conjugation with one or more carbonyl functional groups through one or more carbon-carbon or carbon-nitrogen double bonds.

3. The background electrolyte solution of claim 1 wherein said at least one vinylogous carboxylic acid compound is present as a keto-enol tautomer.

4. The background electrolyte solution of claim 1 wherein said at least one vinylogous carboxylic acid compound is an aromatic compound having a stabilized resonance structure that provides conjugation between one or more hydroxyl groups and one or more carbonyl groups.

5. The background electrolyte solution of claim 1 wherein said at least one vinylogous carboxylic acid compound is a hetero-atom analog of a keto-enol tautomer.

6. The background electrolyte solution of claim 1 wherein said at least one vinylogous carboxylic acid compound is a heteroatom aromatic compound having a stabilized resonance structure that provides conjugation between one or more hydroxyl groups and one or more carbonyl groups.

7. The background electrolyte solution of claim 1 wherein said at least one vinylogous carboxylic acid compound is 3,4-dihydroxy-3-cyclobutene-1,2-dione.

8. The background electrolyte solution of claim 1 wherein said at least one vinylogous carboxylic acid compound is 2,5-dihydroxy-1,4-benzoquinone.

9. The background electrolyte solution of claim 1 wherein said at least one vinylogous carboxylic acid compound is 4,5-dihydroxy-4-cyclopentene-1,2,3-trione.

10. The background electrolyte solution of claim 1 wherein said at least one vinylogous carboxylic acid compound is 5,5-dimethyl-1,3-cyclohexanedione.

11. The background electrolyte solution of claim 1 wherein said at least one vinylogous carboxylic acid compound is 6-hydroxy-1-tetralone.

12. The background electrolyte solution of claim 1 wherein said at least one vinylogous carboxylic acid compound is selected from the group consisting of: 3,4-dihydroxy-3-cyclobutane-1,2-dione; 2,5-dihydroxy-1,4-benzoquinone; 4,5-dihydroxy-4-cyclopentene-1,2,3-trione; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam; 5,5-dimethyl-1,3-cyclohexanedione; tetrahydrofuran-2,4-dione; 6-hydroxy-1-tetralone; 2,3-dihydroxy-2-cyclopropene-1-one; and uric acid.

13. The background electrolyte solution of claim 1 wherein said at least one vinylogous carboxylic acid compound has a vinylogous carboxylic acid UV-chromophore and has a peripheral substituent that does not alter said UV-chromophore.

14. The background electrolyte solution of claim 1 wherein said ions in said sample are anions and are selected from the group consisting of: bromide, carbonate, bicarbonate, chloride, fluoride, nitrate, nitrite, phosphate, sulfate, small molecular weight organic anions, and any combination thereof.

15. The background electrolyte solution of claim 1 wherein said derivative is a cationic enol ester derivative.

16. The background electrolyte solution of claim 15 wherein the ester has the structure:

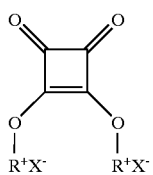

wherein $X^-$ is an ionizable counter ion, and $R^+$ is an organic cation group.

17. The background electrolyte solution of claim 1 wherein said derivative is a cationic enol amide derivative.

18. The background electrolyte solution of claim 17 wherein the amide has the structure:

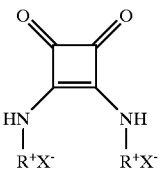

wherein $X^-$ is an ionizable counter ion, and $R^+$ is an organic cation group.

19. The background electrolyte solution of claim 1 wherein said ions in said sample are cations and are selected from the group consisting of: $Na^+$, $K^+$, $Mg^{+2}$, $Ca^{+2}$, small molecular weight organic cations, and any combination thereof.

20. A background electrolyte solution for indirect detection of ions in a sample using capillary electrophoresis, comprising:
    at least one capillary electrophoresis probe that is a vinylogous carboxylic acid compound, or derivative thereof; and
    a buffer.

21. The background electrolyte solution of claim 20 wherein said vinylogous carboxylic acid compound has a structure comprising: one or more enol functional groups in linear conjugation with one or more carbonyl functional groups through one or more carbon-carbon or carbon-nitrogen double bonds.

22. The background electrolyte solution of claim 20 wherein said vinylogous carboxylic acid compound is present as a keto-enol tautomer.

23. The background electrolyte solution of claim 20 wherein said vinylogous carboxylic acid compound is an aromatic compound having a stabilized resonance structure that provides conjugation between one or more hydroxyl groups and one or more carbonyl groups.

24. The background electrolyte solution of claim 20 wherein said vinylogous carboxylic acid compound is a hetero-atom analog of a keto-enol tautomer.

25. The background electrolyte solution of claim 20 wherein said vinylogous carboxylic acid compound is a heteroatom aromatic compound having a stabilized resonance structure that provides conjugation between one or more hydroxyl groups and one or more carbonyl groups.

26. The background electrolyte solution of claim 20 wherein said vinylogous carboxylic acid compound is 3,4-dihydroxy-3-cyclobutene-1,2-dione.

27. The background electrolyte solution of claim 20 wherein said vinylogous carboxylic acid compound is 2,5-dihydroxy-1,4-benzoquinone.

28. The background electrolyte solution of claim 20 wherein said vinylogous carboxylic acid compound is 4,5-dihydroxy-4-cyclopentene-1,2,3-trione.

29. The background electrolyte solution of claim 20 wherein said vinylogous carboxylic acid compound is 2-hydroxy-2,4,6-cycloheptatrienone.

30. The background electrolyte solution of claim 20 wherein said vinylogous carboxylic acid compound is 5,5-dimethyl-1,3-cyclohexanedione.

31. The background electrolyte solution of claim 20 wherein said vinylogous carboxylic acid compound is 6-hydroxy-1-tetralone.

32. The background electrolyte solution of claim 20 wherein said vinylogous carboxylic acid compound is selected from the group consisting of: 3,4-dihydroxy-3-cyclobutane-1,2-dione 2,5-dihydroxy-1,4-benzoquinone;

4,5-dihydroxy-4-cyclopentene-1,2,3-trione; 2-hydroxy-2,4,6-cycloheptatrienone; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4 ketobutyrolactam; 5,5-dimethyl-1,3-cyclohexanedione; tetrahydrofuran-2,4-dione; 6-hydroxy-1-tetralone; 2,3-dihydroxy-2-cyclopropene-1-one; and uric acid.

33. The background electrolyte solution of claim 20 wherein said vinylogous carboxylic acid compound has a vinylogous carboxylic acid UV-chromophore and has a peripheral substituent that does not alter said UV-chromophore.

34. The background electrolyte solution of claim 1 or 20 wherein said background electrolyte solution is provided in a kit for use in a capillary electrophoresis system.

35. The background electrolyte solution of claim 20 wherein the vinylogous carboxylic acid compound is present at a concentration in the range of about 2 to 5 mM.

36. The background electrolyte solution of claim 1 or 20, having a pH in the range of about 7 to 10.

37. The background electrolyte solution of claim 1 or 20, having a pH in the range of 2–3.

38. The background electrolyte solution of claim 20 wherein the buffer is selected from the group consisting of: a tris base, an amine, and an organic base.

39. The background electrolyte solution of claim 1 or 20 additionally comprising a dynamic electroosmotic flow modifier.

40. The background electrolyte solution of claim 39 wherein the dynamic electroosmotic flow modifier is cetyltrimethylammonium bromide or didodecyldimethylammonium bromide.

41. The background electrolyte solution of claim 1 or 20 additionally comprising an organic solvent.

42. The background electrolyte solution of claim 41 wherein the organic solvent is selected from the group consisting of: methanol, ethanol, and acetone.

43. A method of indirectly detecting ions in a sample using capillary electrophoresis, comprising:
introducing a sample into a capillary with a background electrolyte solution comprising one or more capillary electrophoresis probes, wherein at least one of said probes is a vinylogous carboxylic acid compound, or derivative thereof, and a buffer;
applying an electric field along said capillary to cause the ions in the sample to move along said capillary to a detection region and to separate from each other along said capillary; and
detecting the ions indirectly by ultraviolet photometric detection.

44. The method of claim 43 wherein said vinylogous carboxylic acid compound has a structure comprising: one or more enol functional groups in linear conjugation with one or more carbonyl functional groups through one or more carbon-carbon or carbon-nitrogen double bonds.

45. The method of claim 43 wherein said vinylogous carboxylic acid compound is present as a keto-enol tautomer.

46. The method of claim 43 wherein said vinylogous carboxylic acid compound is an aromatic compound having a stabilized resonance structure that provides conjugation between one or more hydroxyl groups and one or more carbonyl groups.

47. The method of claim 43 wherein said vinylogous carboxylic acid compound is a hetero-atom analog of a keto-enol tautomer.

48. The method of claim 43 wherein said vinylogous carboxylic acid compound is a heteroatom aromatic compound having a stabilized resonance structure that provides conjugation between one or more hydroxyl groups and one or more carbonyl groups.

49. The method of claim 43 wherein said vinylogous carboxylic acid compound is 3,4-dihydroxy-3-cyclobutene-1,2-dione.

50. The method of claim 43 wherein said vinylogous carboxylic acid compound is 2,5-dihydroxy-1,4-benzoquinone.

51. The method of claim 43 wherein said vinylogous carboxylic acid compound is 4,5-dihydroxy-4-cyclopentene-1,2,3-trione.

52. The method of claim 43 wherein said vinylogous carboxylic acid compound is 2-hydroxy-2,4,6-cycloheptatrienone.

53. The method of claim 43 wherein said vinylogous carboxylic acid compound is 5,5-dimethyl-1,3-cyclohexanedione.

54. The method of claim 43 wherein said vinylogous carboxylic acid compound is 6-hydroxy-1-tetralone.

55. The method of claim 43 wherein said vinylogous carboxylic acid compound is selected from the group consisting of: 3,4-dihydroxy-3-cyclobutane-1,2-dione; 2,5-dihydroxy-1,4-benzoquinone; 4,5-dihydroxy-4-cyclopentene-1,2,3-trione; 2-hydroxy-2,4,6-cycloheptatrienone; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam; 5,5-dimethyl-1,3-cyclohexanedione; tetrahydrofuran-2,4-dione; roxy-1-tetralone 2,3-dihydroxy-2-cyclopropene-1-one; and uric acid.

56. The method of claim 43 wherein said derivative is a cationic enol ester.

57. The method of claim 56 wherein the ester has the structure:

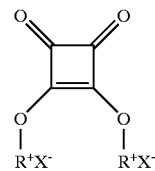

wherein X⁻ is an ionizable counter ion, and R⁺ is an organic cation group.

58. The method of claim 43 wherein said derivative is a cationic enol amide.

59. The method of claim 58 wherein the amide has the structure:

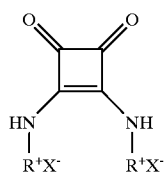

wherein X⁻ is an ionizable counter ion, and R⁺ is an organic cation group.

60. The method of claim 43 wherein said capillary has an interior that is treated to reverse cathodal electro osmotic flow.

61. The method of claim 43 wherein said one or more probes are selected such that ions of differing molecular weight in said sample may be detected by each of said probes.

62. The method of claim 43 wherein said ions are anions.

63. The method of claim 43 wherein said ions are cations, and are selected from the group consisting of: Na$^+$, K$^+$, Mg$^{+2}$, Ca$^{+2}$, small molecular weight organic cations, and any combination thereof.

64. The method of claim 62 wherein said capillary is an anodal capillary and anodal flow of said anions occurs within said capillary.

65. The method of claim 62 wherein said background electrolyte solution includes an electro-osmotic flow modifier and anodal flow of said anions occurs within said capillary, and wherein said one or more probes is of sufficiently high molar absorptivity that its concentration is low enough to avoid precipitating the modifier within the capillary.

66. The method of claim 65 wherein the electro-osmotic flow modifier is cetyltrimethylammonium bromide or didodecyldimethylammonium bromide.

67. The method of claim 43 wherein the background electrolyte solution has a pH in the range of about 7 to 10.

68. The method of claim 43 wherein the background electrolyte solution has a pH in the range of 2–3.

69. The method of claim 43 wherein the buffer is selected from the group consisting of: a tris base, an amine, and an organic base.

70. The method of claim 43 wherein the vinylogous carboxylic acid compound has a concentration of about 2 to 5 mM.

71. The method of claim 43 wherein the background electrolyte solution additionally comprises an organic solvent.

72. The method of claim 71 wherein the organic solvent is selected from the group consisting of: methanol, ethanol, and acetone.

73. A capillary electrophoresis apparatus for indirectly detecting ions in a sample, comprising:
   a capillary having a background electrolyte solution comprising one or more capillary electrophoresis probes that is a vinylogous carboxylic acid compound, or derivative thereof, and a buffer;
   an electrical source that is configured to apply an electric field along said capillary to cause the ions to move and to separate from each other along said capillary to a detection region; and
   a detector that is configured to detect the ions by indirect ultraviolet photometric detection.

74. The apparatus of claim 73 wherein said vinylogous carboxylic acid compound has a structure comprising: one or more enol functional groups in linear conjugation with one or more carbonyl functional groups through one or more carbon-carbon or carbon-nitrogen double bonds.

75. The apparatus of claim 73 wherein said vinylogous carboxylic acid compound is present as a keto-enol tautomer.

76. The apparatus of claim 73 wherein said vinylogous carboxylic acid compound is an aromatic compound having a stabilized resonance structure that provides conjugation between one or more hydroxyl groups and one or more carbonyl groups.

77. The apparatus of claim 73 wherein said vinylogous carboxylic acid compound is a hetero-atom analog of a keto-enol tautomer.

78. The apparatus of claim 73 wherein said vinylogous carboxylic acid compound is a heteroatom aromatic compound having a stabilized resonance structure that provides conjugation between one or more hydroxyl groups and one or more carbonyl groups.

79. The apparatus of claim 73 wherein said vinylogous carboxylic acid compound is 3,4-dihydroxy-3-cyclobutene-1,2-dione.

80. The apparatus of claim 73 wherein said vinylogous carboxylic acid compound is 2,5-dihydroxy-1,4-benzoquinone.

81. The apparatus of claim 73 wherein said vinylogous carboxylic acid compound is 4,5-dihydroxy-4-cyclopentene-1,2,3-trione.

82. The apparatus of claim 73 wherein said vinylogous carboxylic acid compound is 2-hydroxy-2,4,6-cycloheptatrienone.

83. The apparatus of claim 73 wherein said vinylogous carboxylic acid compound is 5,5-dimethyl-1,3-cyclohexanedione.

84. The apparatus of claim 73 wherein said vinylogous carboxylic acid compound is 6-hydroxy-1-tetralone.

85. The apparatus of claim 73 wherein said vinylogous carboxylic acid compound is selected from the group consisting of: 3,4-dihydroxy-3-cyclobutane-1,2-dione; 2,5-dihydroxy-1,4-benzoquinone; 4,5-dihydroxy-4-cyclopentene-1,2,3-trione; 2-hydroxy-2,4,6-cycloheptatrienone, 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam; 5,5-dimethyl-1,3-cyclohexanedione; tetrahydrofuran-2,4-dione; 6-hydroxy-1-tetralone; 2,3-dihydroxy-2-cyclopropene-1-one; and uric acid.

86. The apparatus of claim 73 wherein said derivative is a cationic enol ester.

87. The apparatus of claim 86 wherein the ester has the structure:

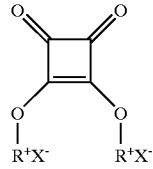

wherein X$^-$ is an ionizable counter ion, and R$^+$ is an organic cation group.

88. The apparatus of claim 73 wherein said derivative is a cationic enol amide.

89. The apparatus of claim 88 wherein the amide has the structure:

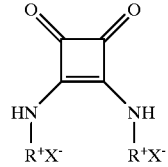

wherein X$^-$ is an ionizable counter ion, and R$^+$ is an organic cation group.

90. The apparatus of claim 73 wherein the vinylogous carboxylic acid compound has a concentration of about 2 to 5 mM.

91. The apparatus of claim 73 wherein the background electrolyte solution has a pH in the range of about 7 to 10.

92. The apparatus of claim 73 wherein the background electrolyte solution has a pH in the range of 2–3.

93. The apparatus of claim 73 wherein the buffer is selected from the group consisting of: a tris base, an amine, and an organic base.

94. The apparatus of claim 73 additionally comprising a dynamic electroosmotic flow modifier.

95. The apparatus of claim 94 wherein the electroosmotic flow modifier is cetyltrimethylammonium bromide or didodecyldimethylammonium bromide.

96. The apparatus of claim 73 wherein the background electrolyte solution additionally comprises an organic solvent.

97. The apparatus of claim 96 wherein the organic solvent is selected from the group consisting of: methanol, ethanol, and acetone.

98. A kit for indirectly detecting ions in a sample by capillary electrophoresis, comprising:
a background electrolyte solution comprising one or more capillary electrophoresis probes that is a vinylogous carboxylic acid compound, or derivative thereof, and a buffer.

99. The kit of claim 98 wherein said vinylogous carboxylic acid compound has a structure comprising: one or more enol functional groups in linear conjugation with one or more carbonyl functional groups through one or more carbon-carbon or carbon-nitrogen double bonds.

100. The kit of claim 98 wherein said vinylogous carboxylic acid compound is present as a keto-enol tautomer.

101. The kit of claim 98 wherein said vinylogous carboxylic acid compound is an aromatic compound having a stabilized resonance structure that provides conjugation between one or more hydroxyl groups and one or more carbonyl groups.

102. The kit of claim 98 wherein said vinylogous carboxylic acid compound is a hetero-atom analog of a keto-enol tautomer.

103. The kit of claim 98 wherein said vinylogous carboxylic acid compound is a heteroatom aromatic compound having a stabilized resonance structure that provides conjugation between one or more hydroxyl groups and one or more carbonyl groups.

104. The kit of claim 98 wherein said vinylogous carboxylic acid compound is 3,4-dihydroxy-3-cyclobutene-1,2-dione.

105. The kit of claim 98 wherein said vinylogous carboxylic acid compound is 2,5-dihydroxy-1,4-benzoquinone.

106. The kit of claim 98 wherein said vinylogous carboxylic acid compound is 4,5-dihydroxy-4-cyclopentene-1,2,3-trione.

107. The kit of claim 98 wherein said vinylogous carboxylic acid compound is 2-hydroxy-2,4,6-cycloheptatrienone.

108. The kit of claim 98 wherein said vinylogous carboxylic acid compound is 5,5-dimethyl-1,3-cyclohexanedione.

109. The kit of claim 98 wherein said vinylogous carboxylic acid compound is 6-hydroxy-1-tetralone.

110. The kit of claim 98 wherein said vinylogous carboxylic acid compound is selected from the group consisting of: 3,4-dihydroxy-3-cyclobutane-1,2-dione 2,5-dihydroxy-1,4-benzoquinone; 4,5-dihydroxy-4-cyclopentene-1,2,3-trione; 2-hydroxy-2,4,6-cycloheptatrienone; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam, 5,5-dimethyl-1,3-cyclohexanedione; tetrahydrofuran-2,4-dione; 6-hydroxy-1-tetralone; 2,3-dihydroxy-2-cyclopropene-1-one; and uric acid.

111. The kit of claim 98 wherein said derivative is a cationic enol ester.

112. The kit of claim 111 wherein the ester has the structure:

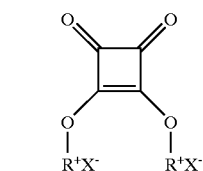

wherein $X^-$ is an ionizable counter ion, and $R^+$ is an organic cation group.

113. The kit of claim 98 wherein said derivative is a cationic enol amide.

114. The kit of claim 113 wherein the amide has the structure:

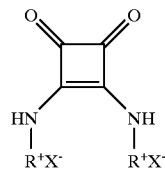

wherein $X^-$ is an ionizable counter ion, and $R^+$ is an organic cation group.

115. The kit of claim 98 wherein the vinylogous carboxylic acid compound has a concentration of about 2 to 5 mM.

116. The kit of claim 98 wherein the background electrolyte solution has a pH in the range of about 7 to 10.

117. The kit of claim 98 wherein the background electrolyte solution has a pH in the range of 2–3.

118. The kit of claim 98 wherein the buffer is selected from the group consisting of: a tris base, an amine, and an organic base.

119. The kit of claim 98 additionally comprising a dynamic electroosmotic flow modifier.

120. The kit of claim 119 wherein the electroosmotic flow modifier is cetyltrimethylammonium bromide or didodecyldimethylammonium bromide.

121. The kit of claim 98 wherein the background electrolyte additionally comprises an organic solvent.

122. The kit of claim 121 wherein the organic solvent is selected from the group consisting of: methanol, ethanol, and acetone.

123. A method of indirectly detecting ions in a sample using capillary electrophoresis, comprising:
introducing the sample into a capillary with a background electrolyte solution containing one or more capillary electrophoresis probes that is a vinylogous carboxylic acid compound, or derivative thereof, wherein said vinylogous carboxylic acid compound is not tropolone;
applying an electric field along said capillary to cause the ions in the sample to move and to separate along said capillary to a detection region; and
detecting the ions indirectly by ultraviolet photometric detection.

124. The method of claim 123, wherein said vinylogous carboxylic acid compound has a concentration of about 2 to 5 mM.

125. A capillary electrophoresis apparatus for indirectly detecting ions in a sample, comprising:
a capillary having a background electrolyte solution containing one or more capillary electrophoresis probes that is a vinylogous carboxylic acid compound, or derivative thereof, wherein said vinylogous carboxylic acid compound is not tropolone;

an electrical source which applies an electric field along said capillary to cause the ions to move and to separate along said capillary to a detection region; and a detector which detects the ions by indirect ultraviolet photometric detection.

126. The apparatus of claim 125, wherein said vinylogous carboxylic acid compound has a concentration of about 2 to 5 mM.

127. A kit for indirectly detecting ions in a sample by capillary electrophoresis, comprising:

a background electrolyte solution containing one or more capillary electrophoresis probes that is a vinylogous carboxylic acid compound, or derivative thereof, wherein said vinylogous carboxylic acid compound is not tropolone.

128. The kit of claim 127, wherein said vinylogous carboxylic acid compound has a concentration of about 2 to 5 mM.

129. A background electrolyte solution for detecting small molecular weight ions in a sample using capillary electrophoresis comprising:

a probe that is comprised of at least one vinylogous carboxylic acid compound or derivative thereof in a concentration of about 2 to 5 mM, wherein said vinylogous carboxylic acid compound is not tropolone and wherein said probe has an electrophoretic mobility comparable to the ions.

130. The background electrolyte solution of claim 129 wherein said at least one vinylogous carboxylic acid compound is 3,4-dihydroxy-3-cyclobutene-1,2-dione.

131. A background electrolyte solution of any one of claims 1, 20, 129, and 130 wherein the ions are present at about 500 ppt in the sample.

132. A background electrolyte solution of any one of claims 1, 20, 129, and 130 wherein the ions are present between 80 and 320 ppb in the sample.

133. A background electrolyte solution of any one of claims 1, 20, 129, and 130 wherein said vinylogous carboxylic acid compound exhibits absorption in the UV spectrum at wavelengths of about 270 nm and higher.

134. The background electrolyte solution of claim 129 wherein said at least one vinylogous carboxylic acid compound is selected from the group consisting of: 3,4-dihydroxy-3-cyclobutane-1,2-dione; 2,5-dihydroxy-1,4-benzoquinone; 4,5-dihydroxy-4-cyclopentene-1,2,3-trione; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam; 5,5-dimethyl-1,3-cyclohexanedione; tetrahydrofuran-2,4-dione; 6-hydroxy-1-tetralone; 2,3-dihydroxy-2-cyclopropene-1-one; and uric acid.

135. The background electrolyte solution of claim 129 wherein said at least one vinylogous carboxylic acid compound has a vinylogous carboxylic acid UV-chromophore and has a peripheral substituent that does not alter said UV-chromophore.

136. The background electrolyte solution of claim 129 wherein said ions in said sample are anions and are selected from the group consisting of: bromide, carbonate, bicarbonate, chloride, fluoride, nitrate, nitrite, phosphate and sulfate and small molecular weight organic anions.

137. The background electrolyte solution of claim 129 wherein said ions in said sample are cations and are selected from the group consisting of: $Na^+$, $K^+$, $Mg^{+2}$, $Ca^{+2}$, and small molecular weight organic cations, and any combination thereof.

138. The background electrolyte solution of claim 129 wherein said derivative is a cationic enol ester derivative.

139. The background electrolyte solution of claim 129 wherein said derivative is a cationic enol amide derivative.

140. A background electrolyte solution of claim 139 wherein the vinylogous carboxylic acid compound exhibits absorption in the UV spectrum at wavelengths of between 270 and 320 nm.

141. A background electrolyte solution for indirect detection of small molecular weight ions in a sample using capillary electrophoresis, comprising:

at least one probe that is a vinylogous carboxylic acid compound, or derivative thereof, wherein said probe has an electrophoretic mobility comparable to the ions; and a buffer.

142. The background electrolyte solution of claim 141 wherein said vinylogous carboxylic acid compound is 3,4-dihydroxy-3-cyclobutene-1,2-dione.

143. The background electrolyte solution of claim 141 wherein said vinylogous carboxylic acid compound is selected from the group consisting of: 3,4-dihydroxy-3-cyclobutane-1,2-dione; 2,5-dihydroxy-1,4-benzoquinone; 4,5-dihydroxy-4-cyclopentene-1,2,3-trione; 2-hydroxy-2,4,6-cycloheptatrienone; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam, 5,5-dimethyl-1,3-cyclohexanedione; tetrahydrofuran-2,4-dione, 6-hydroxy-1-tetralone; 2,3-dihydroxy-2-cyclopropene-1-one; and uric acid.

144. The background electrolyte solution of claim 141 wherein said vinylogous carboxylic acid compound has a vinylogous carboxylic acid UV-chromophore and has a peripheral substituent that does not alter said UV-chromophore.

145. The background electrolyte solution of claim 141 wherein said ions in said sample are anions and are selected from the group consisting of: bromide, carbonate, bicarbonate, chloride, fluoride, nitrate, nitrite, phosphate, sulfate, and small molecular weight organic anions, and any combination thereof.

146. The background electrolyte solution of claim 141 wherein said ions in said sample are cations and are selected from the group consisting of: $Na^+$, $K^+$, $Mg^{+2}$, $Ca^{+2}$, and small molecular weight organic cations, and any combination thereof.

147. The background electrolyte solution of claim 141 wherein said derivative is a cationic enol ester derivative.

148. The background electrolyte solution of claim 141 wherein said derivative is a cationic enol amide derivative.

149. A method of indirectly detecting small molecular weight ions in a sample using capillary electrophoresis, comprising:

introducing a sample into a capillary with a background electrolyte solution containing one or more probes wherein at least one of said probes is a vinylogous carboxylic acid compound, or derivative thereof, wherein said probe has an electrophoretic mobility comparable to the ions, and a buffer;

applying an electric field along said capillary to cause the ions in the sample to move along said capillary to a detection region and to separate from each other along said capillary; and detecting the ions indirectly by ultraviolet photometric detection.

150. The method of claim 149 wherein said at least one vinylogous carboxylic acid compound is 3,4-dihydroxy-3-cyclobutene-1,2-dione.

151. The method of claim 149 wherein said vinylogous carboxylic acid compound is selected from the group consisting of: 3,4-dihydroxy-3-cyclobutane-1,2-dione; 2,5-dihydroxy-1,4-benzoquinone; 4,5-dihydroxy-4-cyclopentene-1,2,3-trione; 2-hydroxy-2,4,6-cycloheptatrienone; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam; 5,5-dimethyl-1,3-cyclohexanedione; tetrahydrofuran-2,4-dione; 6-hydroxy-1-tetralone, 2,3-dihydroxy-2-cyclopropene-1-one; and uric acid.

152. The method of claim 149 wherein said vinylogous carboxylic acid compound has a vinylogous carboxylic acid UV-chromophore and has a peripheral substituent that does not alter said UV-chromophore.

153. The method of claim 149 wherein said ions in said sample are anions and are selected from the group consisting of: bromide, carbonate, bicarbonate, chloride, fluoride, nitrate, nitrite, phosphate, sulfate, and small molecular weight organic anions, and any combination thereof.

154. The method of claim 149 wherein said ions in said sample are cations and are selected from the group consisting of: $Na^+$, $K^+$, $Mg^{+2}$, $Ca^{+2}$, and small molecular weight organic cations, and any combination thereof.

155. The method of claim 149 wherein said derivative is a cationic enol ester derivative.

156. The method of claim 149 wherein said derivative is a cationic enol amide derivative.

157. A capillary electrophoresis apparatus for indirectly detecting small molecular weight ions in a sample, comprising:
a capillary having a background electrolyte solution containing one or more probes that is a vinylogous carboxylic acid compound, or derivative thereof, wherein said probe has an electrophoretic mobility comparable to the ions, and a buffer;
an electrical source that is configured to apply an electric field along said capillary to cause the ions to move and to separate from each other along said capillary to a detection region; and
a detector that is configured to detect the ions by indirect ultraviolet photometric detection.

158. The apparatus of claim 157 wherein said vinylogous carboxylic acid compound is 3,4-dihydroxy-3-cyclobutene-1,2-dione.

159. The apparatus of claim 157 wherein said vinylogous carboxylic acid compound is selected from the group consisting of: 3,4-dihydroxy-3-cyclobutane-1,2-dione; 2,5-dihydroxy-1,4-benzoquinone; 4,5-dihydroxy-4-cyclopentene-1,2,3-trione; 2-hydroxy-2,4,6-cycloheptatrienone; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam; 5,5-dimethyl-1,3-cyclohexanedione; tetrahydrofuran-2,4-dione; 6-hydroxy-1-tetralone; 2,3-dihydroxy-2-cyclopropene-1-one; and uric acid.

160. The apparatus of claim 157 wherein said vinylogous carboxylic acid compound has a vinylogous carboxylic acid UV-chromophore and has a peripheral substituent that does not alter said UV-chromophore.

161. The apparatus of claim 157 wherein said ions in said sample are anions and are selected from the group consisting of: bromide, carbonate, bicarbonate, chloride, fluoride, nitrate, nitrite, phosphate and sulfate and small molecular weight organic anions.

162. The apparatus of claim 157 wherein said ions in said sample are cations and are selected from the group consisting of: $Na^+$, $K^+$, $Mg^{+2}$, $Ca^{+2}$, and small molecular weight organic cations.

163. The apparatus of claim 157 wherein said derivative is a cationic enol ester derivative.

164. The apparatus of claim 157 wherein said derivative is a cationic enol amide derivative.

165. A kit for indirectly detecting small molecular weight ions in a sample by capillary electrophoresis, comprising:
a background electrolyte solution comprising one or more probes that is a vinylogous carboxylic acid compound, or derivative thereof, wherein said probe has an electrophoretic mobility comparable to the ions, and a buffer.

166. The kit of claim 165 wherein said vinylogous carboxylic acid compound is 3,4-dihydroxy-3-cyclobutene-1,2-dione.

167. The kit of claim 165 wherein said vinylogous carboxylic acid compound is selected from the group consisting of: 3,4-dihydroxy-3-cyclobutane-1,2-dione; 2,5-dihydroxy-1,4-benzoquinone; 4,5-dihydroxy-4-cyclopentene-1,2,3-trione; 2-hydroxy-2,4,6-cycloheptatrienone; 5,6-dihydroxy-5-cyclohexane-1,2,3,4-tetraone; 2-hydroxy-1,4-naphthoquinone; 3-oxo-1-gulofuranolactone; 2,2-dimethyl-1,3-dioxane-4,6-dione; 4-ketobutyrolactam; 5,5-dimethyl-1,3-cyclohexanedione; tetrahydrofuran-2,4-dione; 6-hydroxy-1-tetralone; 2,3-dihydroxy-2-cyclopropene-1-one; and uric acid.

168. The kit of claim 165 wherein said vinylogous carboxylic acid compound has a vinylogous carboxylic acid UV-chromophore and has a peripheral substituent that does not alter said UV-chromophore.

169. The kit of claim 165 wherein said ions in said sample are anions and are selected from the group consisting of: bromide, carbonate, bicarbonate, chloride, fluoride, nitrate, nitrite, phosphate, sulfate, and small molecular weight organic anions, and any combination thereof.

170. The kit of claim 165 wherein said ions in said sample are cations and are selected from the group consisting of: $Na^+$, $K^+$, $Mg^{+2}$, $Ca^{+2}$, and small molecular weight organic cations, and any combination thereof.

171. The kit of claim 165 wherein said derivative is a cationic enol ester derivative.

172. The kit of claim 165 wherein said derivative is a cationic enol amide derivative.

* * * * *